US009205014B1

(12) United States Patent
Nesley

(10) Patent No.: US 9,205,014 B1
(45) Date of Patent: Dec. 8, 2015

(54) HEIGHT-ADJUSTABLE PILLOW FOR USE IN SURGERY

(71) Applicant: Todd Nesley, Martinez, GA (US)

(72) Inventor: Todd Nesley, Martinez, GA (US)

( * ) Notice: Subject to any disclaimer, the term of this patent is extended or adjusted under 35 U.S.C. 154(b) by 0 days.

(21) Appl. No.: 14/321,637

(22) Filed: Jul. 1, 2014

(51) Int. Cl.
*A61F 5/37* (2006.01)
*A61G 13/12* (2006.01)
*A47G 9/10* (2006.01)

(52) U.S. Cl.
CPC ............ *A61G 13/121* (2013.01); *A47G 9/1027* (2013.01); *A61G 13/129* (2013.01); *A47G 2009/1018* (2013.01)

(58) Field of Classification Search
CPC .................................. A47C 27/10; A61F 5/37
USPC ...................... 5/621–624, 636–637, 640, 644
See application file for complete search history.

(56) References Cited

U.S. PATENT DOCUMENTS

| | | | | |
|---|---|---|---|---|
| 3,762,404 | A | 10/1973 | Sakita | |
| 5,363,524 | A | 11/1994 | Lang | |
| 6,751,818 | B2 | 6/2004 | Troop | |
| 6,935,340 | B2 | 8/2005 | Saied | |
| 7,681,262 | B2 | 3/2010 | Weedling et al. | |
| 7,716,763 | B2 | 5/2010 | Nissen et al. | |
| 8,690,807 | B2 | 4/2014 | Hiebert | |
| 2011/0191960 | A1 * | 8/2011 | Hiebert | 5/615 |
| 2014/0208513 | A1 | 7/2014 | Hiebert | |

OTHER PUBLICATIONS

Copenheaver, Blaine, International Search Report and the Written Opinion of the International Searching Authority, or Declaration, dated Sep. 17, 2015, Applicant Name: Nesley, Todd, International Application No. PCT/US2015/038878; International Filing date Jul. 1, 2015.

* cited by examiner

*Primary Examiner* — Fredrick Conley
(74) *Attorney, Agent, or Firm* — John C. Cave; Gunn, Lee & Cave, P.C.

(57) ABSTRACT

A height-adjustable pillow for supporting a patient's head. The pillow includes a casing of flexible material defining a casing volume and a volume of filler material partially occupying in said casing volume. The casing volume is compressible and expandable. The casing volume includes a support portion positioned above a base portion. An air valve is associated with the casing for introducing air into and evacuating air from said casing volume.

17 Claims, 5 Drawing Sheets

HEIGHT-ADJUSTABLE PILLOW FOR USE IN SURGERY

CROSS-REFERENCES TO RELATED APPLICATIONS

Not applicable.

STATEMENT REGARDING FEDERALLY-SPONSORED RESEARCH OR DEVELOPMENT

Not applicable.

BACKGROUND OF THE INVENTION

1. Field of the Invention

The present invention relates to medical devices. More specifically, the present invention is a height-adjustable pillow for supporting the head of patient during a medical procedure.

2. Description of the Related Art

In the field of surgical headrests, the current approach to position a patient's head for a surgical procedure using standard, one-size-fits-all pillows, despite that patients come in all sizes and shapes from pediatrics to the largest of patients. Such headrests complicate the airway management process by facilitating a difficult view of the larynx. This demands extraordinary maneuvers by a healthcare provider to secure the airway.

SUMMARY OF THE INVENTION

The present invention is a height-adjustable pillow for supporting a patient's head, either directly or with a headrest. The pillow includes a casing of flexible material defining a casing volume and a volume of filler material partially occupying the casing volume. The casing volume is compressible and expandable and includes a support portion positioned above a base portion. The base portion defines a first volume. The support portion defines a second volume. An opening between the support position and the base portion allows the filler material to pass between the volumes. An air valve is associated with the casing for introducing air into and evacuating air from said casing volume.

The present invention also provides a method of adjusting and supporting the position of a patient's head with an adjustable pillow. The method includes the steps of positioning a casing below a patient's head, the casing having a base portion having a first volume and a support portion having a second volume; introducing filler material into the casing; introducing air into the casing; compressing the first volume; and moving the filler material from said first volume into said second volume.

The present invention places every patient in the perfect ramped-up, sniffing position, thereby lining up the patient's laryngeal axis, the pharyngeal axis, and the axis of the mouth completely independent of the patient's body mass index. The present invention can be molded to support the patient in the lateral and the prone position specific to individual patient habitus. This application of correct anatomical positioning for airway management improves the ability of the healthcare provider to secure the airway and thus improves patient care by causing less stress and trauma to the patient's throat. Moreover, the invention improves the provider's ability to secure a "difficult" airway.

In addition, the present invention has a lower economical and environmental cost. For one, the present invention allows a single apparatus that customizes to the height of the small prone headrest. Competitors, however, often use nine inches of foam as a prone pillow, which is more expensive than embodiments of the present invention. Moreover, because of the great difference in headrest size, the various embodiments of the invention, along with the prone headrest, have smaller ecological footprints in landfills when ultimately discarded.

DETAILED DESCRIPTION OF THE INVENTION

Figure 1:
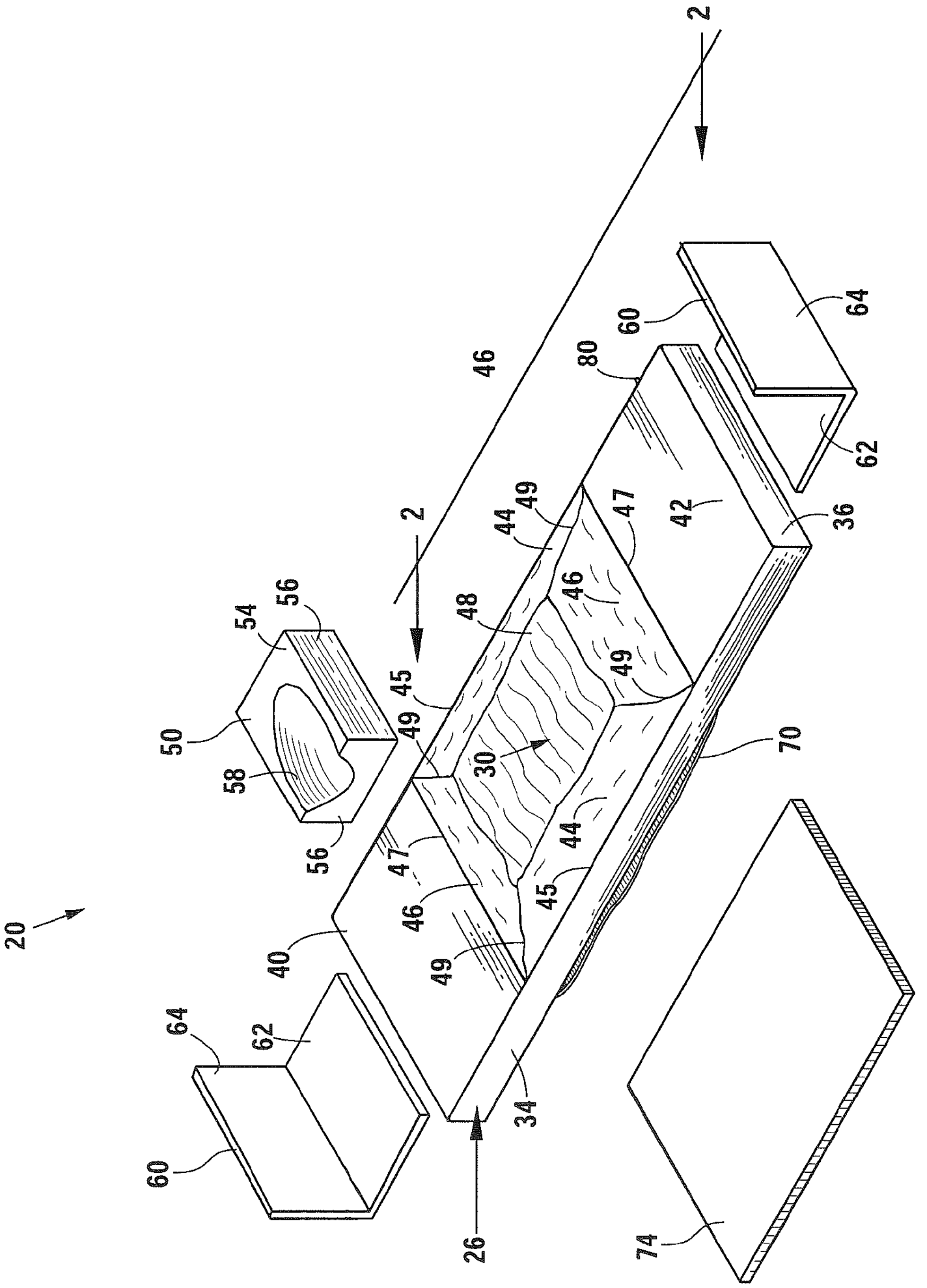
FIG. 1 is an isometric view of an embodiment of the present invention.
Figure 2:
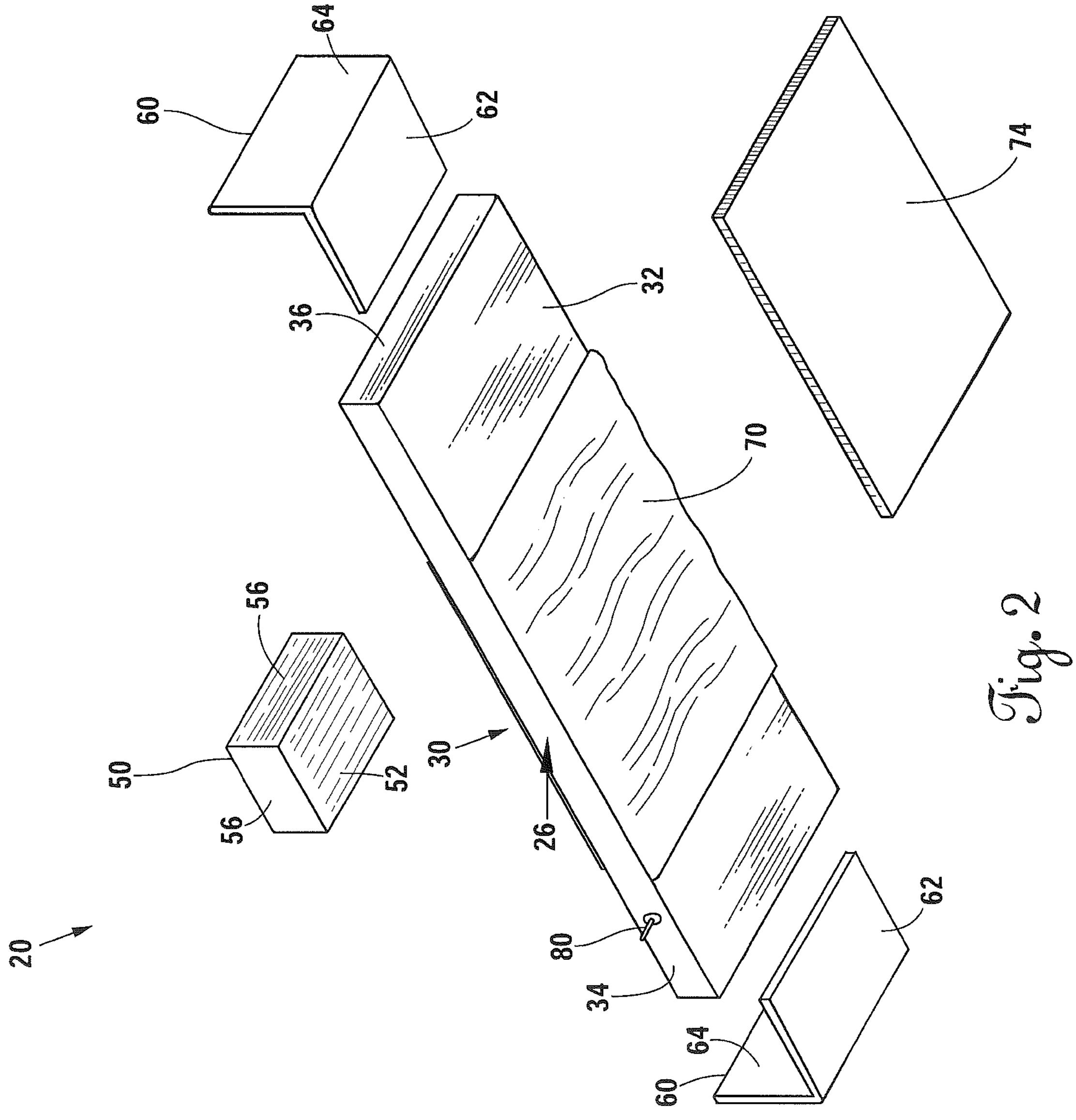
FIG. 2 is a reverse isometric view of the embodiment.

FIGS. 1-2 show a first embodiment 20 having the features of the present invention. The embodiment 20 includes a casing 22 made of pieces of flexible material connected together. Preferably, the flexible material is PVC Tarpaulin having a 0.4 mm thickness, with the pieces being heat-welded together. However, other methods of connecting the pieces of flexible material may be used.

The casing 22 includes is a base portion 26 and a support portion 30. Preferably, the base portion 26 has a generally-rectangular cuboid shape formed of a generally rectangular bottom 32 (see FIG. 2) and four sidewalls. The four sidewalls include a first pair of opposing sidewalls 34 and a second pair of opposing sidewalls 36. Each sidewall 34, 36 has the same height. Each of the first pair of sidewalls 34 has a first length L1. Each of the second pair of sidewalls has a second length L2. Referring specifically to FIG. 1, first and second top pieces 40, 42 are each attached to the first pair of sidewalls 34 and one of the second pair of sidewalls 36. Referring specifically to FIG. 2, the bottom 32 is attached to the first pair and second pair of sidewalls 34, 36.

The support portion 30 is made up of a first pair of trapezoidal pieces 44, a second pair of trapezoidal pieces 46, and a top piece 48. Each of the first pair of trapezoidal pieces 44 has a bottom edge 45 attached to the first pair of sidewalls 34 opposite the bottom 32. Each of the second pair of trapezoidal pieces 46 has side edges 49 attached to the first pair of trapezoidal pieces 44 and bottom edges 47 attached to the first and second top pieces 40, 42. The top piece is attached to the small bases of the trapezoidal pieces 46, 48.

The preferred embodiment 20 may include a headrest 50 having a planar bottom surface 52 (see FIG. 2), a planar top surface 54, and side surfaces 56 adjacent to, and at a right angle from, the bottom surface 52 and top surface 54. A concave curved surface 58 adjacent to the top surface 54 and one side surface 56. The headrest is preferably made from a foam or other soft material.

The preferred embodiment 20 may include two side panels 60 positioned outside and adjacent one of the pairs of opposing sidewalls 36. Each side panel 60 is made of a rigid material, such as steel or hard plastic, and has an L-shaped profile formed from a bottom plate 62 attached to a side plate 64 at a right angle.

The preferred embodiment 20 may include a material piece 70 attached to the bottom 32, to form a pocket. A support plate 74 is positioned below and adjacent the base portion 26 within the pocket. Preferably the support plate 74 is a piece of polypropylene plastic, but may be any other rigid material.

An air valve 80 may be attached to one of the sidewalls 34. The air valve 80 establishes a normally-closed but selectively-openable fluid communication path through the casing 22.

Figure 3:
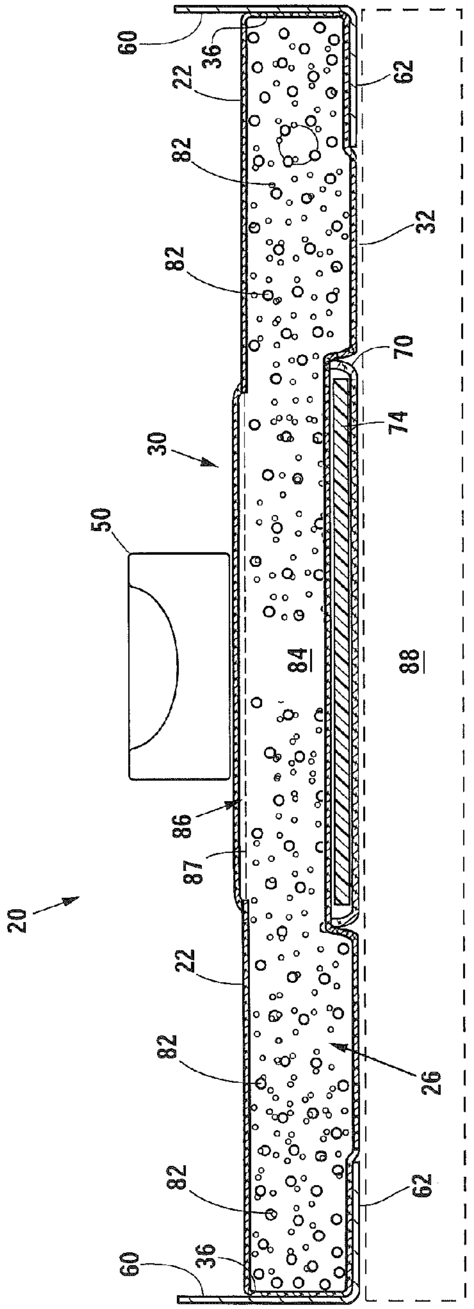
FIG. 3 is a partial sectional view of the embodiment in a first state.

FIG. 3 shows the embodiment 20 in a first state and positioned on a table 88. The side panels 60 are in contact with the second pair of sidewalls 36. The support plate 74 is within the pocket formed between the bottom 32 and material piece 70. The base portion 26 has a first volume 84 and the support portion 30 has a second volume 86. An opening 87 extends between the first volume 84 and the second volume 86. Collectively, the first volume 84 and second volume 86 make up an enclosed casing volume.

The casing 22 contains air and a volume of filler material 82 made up of polystyrene beads and plastic beads. Preferably, the ratio of polystyrene beads to plastic beads is seven to three. In FIG. 3, the filler only occupies the first volume 84. In this first state, the base portion 26 is fully expanded and the support portion 30 is fully compressed.

Figure 4:
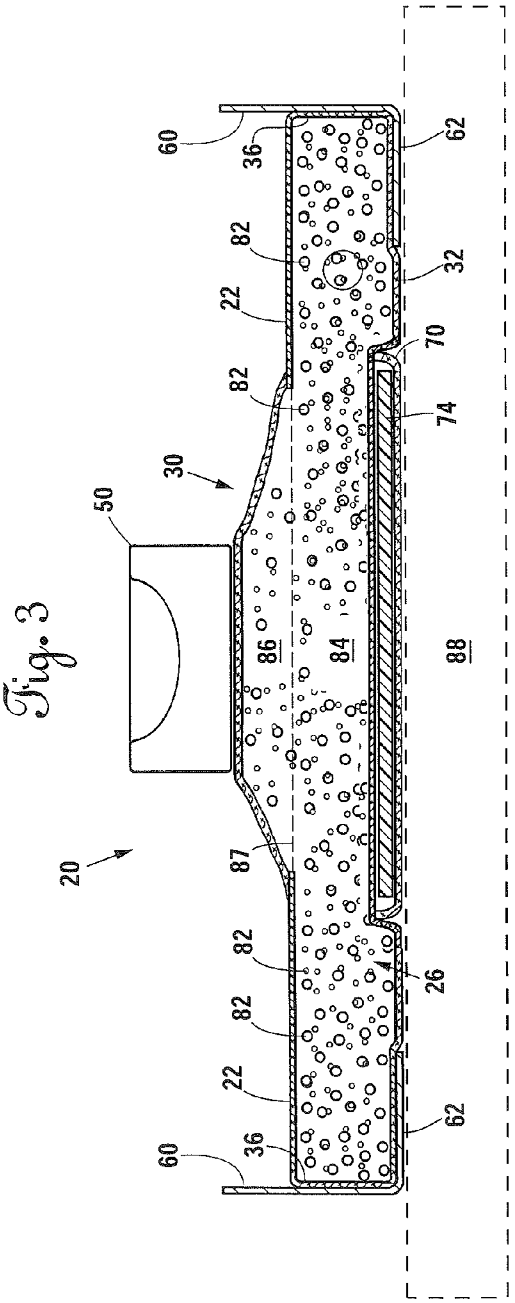
FIG. 4 is a partial sectional view of the embodiment in a second state.

FIG. 4 shows the embodiment 20 in a second state where the length of the base portion is less than in the first state. Thus, the magnitude of the first volume in FIG. 4 is less than the magnitude of the first volume shown in FIG. 3. Some of the filler material 82 occupies the second portion 86.

Figure 5:
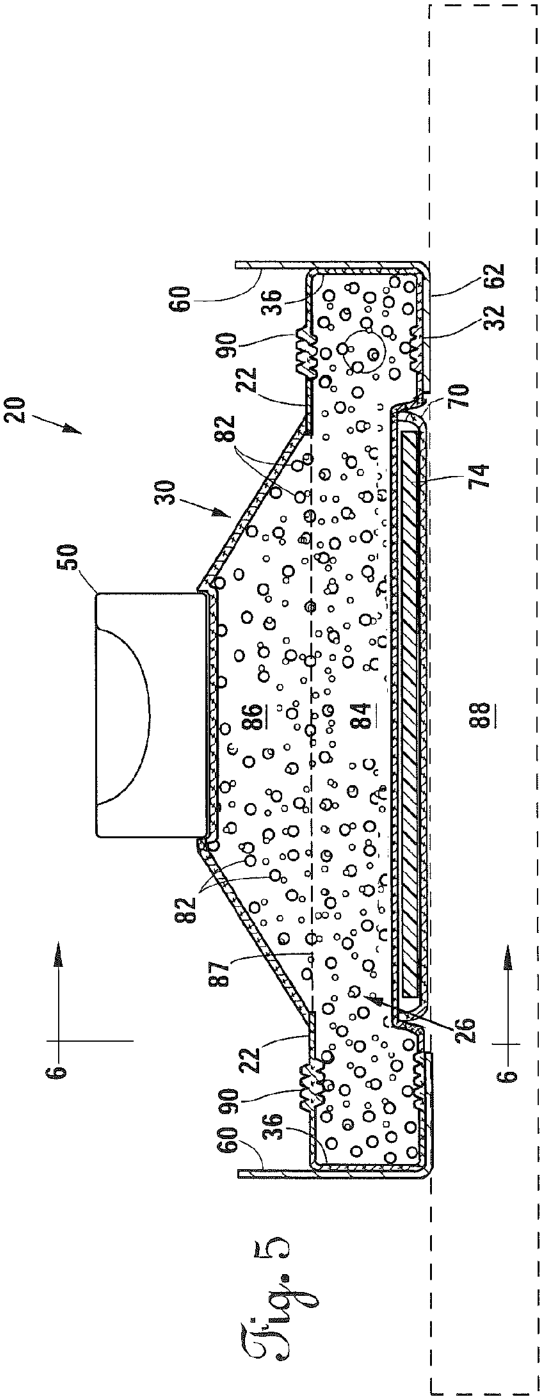
FIGS. 5-6 are partial sectional views of the embodiment in a third state.
Figure 6:
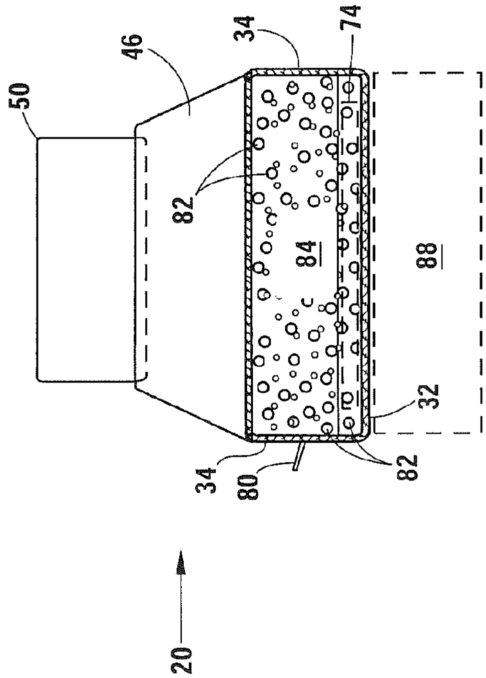

FIGS. 5-6 show the embodiment 20 in a third state wherein the support portion 30 is fully expanded into the general shape of a frustum and air has been evacuated from the casing through the air valve 80. The magnitude of the first volume 84 in FIGS. 5 and 6 is less than the magnitude of the first volume shown in FIG. 4 because of further compression of the base portion 26, which causes folds 90 in the casing 22. Notably, the user may select any position between the first and third states shown in FIG. 3 and FIG. 5, respectively, depending on the preference of the user and needed positioning of the patient.

Use of the embodiment 20 is initially described with reference to FIG. 3, with the casing 22 containing the filler material 82 and air. The casing 22 is positioned below a headrest 50 and on a table 88. The side panels 60 are positioned adjacent to the second pair of sidewalls 36 with the bottom plates 62 in contact with the bottom 32 of the casing 22.

Referring to FIG. 4, the side panels 60 are moved inward causing the length of the base portion 26 to decrease and therefore the magnitude of the first volume 84 to decrease. A portion of the filler material 82 is thereby displaced through the opening 87 into the second volume 86 causing the second volume 86 to expand and thereby causing the position of the top piece 48 of the support portion to be raised. This, in turn, lifts the headrest 50 away from the table 88.

Referring to the FIGS. 5-6, the side panels are moved further inward to a third state causing compression of the first volume 84, which, in turn, causes a larger quantity of filler material 82 to move through the opening 87 into the second volume 86. As a result, second volume 84 is expanded further (relative to FIG. 4) and the top piece 48 of the support portion 50 is raised further. This, in turn, causes the headrest 50 to raise further.

Alternative embodiments may not include the side panels 60. In such embodiments the base portion 26 is longitudinally compressed directly by the practitioner.

The headrest 50 may be selectively positioned anywhere between the first state shown in FIG. 3 and the third state shown in FIGS. 5-6 depending on the user's preference. When the desired head position is obtained, air is evacuated from the casing 22 through the air valve 80. The resultant different of pressure between the outside and inside of the casing 22 forces the casing 22 against the filler 82 and causes the casing 22 to hold its shape. This results in a frictional engagement of the top piece 48 with the bottom surface 52 and possibly the side surfaces 56 of the headrest 50, which frictional engagement inhibits movement of the headrest 50 relative to the casing 22. If a position change is later desired, air can be reintroduced into the casing 22 to equalize the inside and outside pressure, allowing the filler to be moved between volumes to change the height of the headrest 50.

Figure 7:
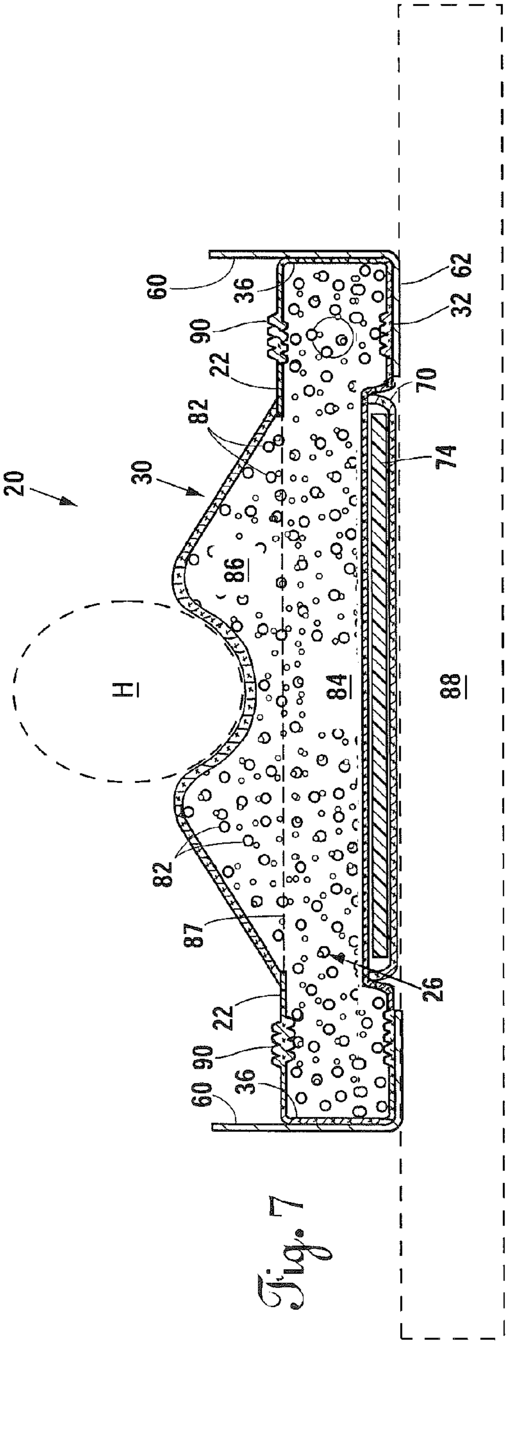
FIG. 7 is a partial sectional view of the embodiment in a fourth state.
Figure 8:
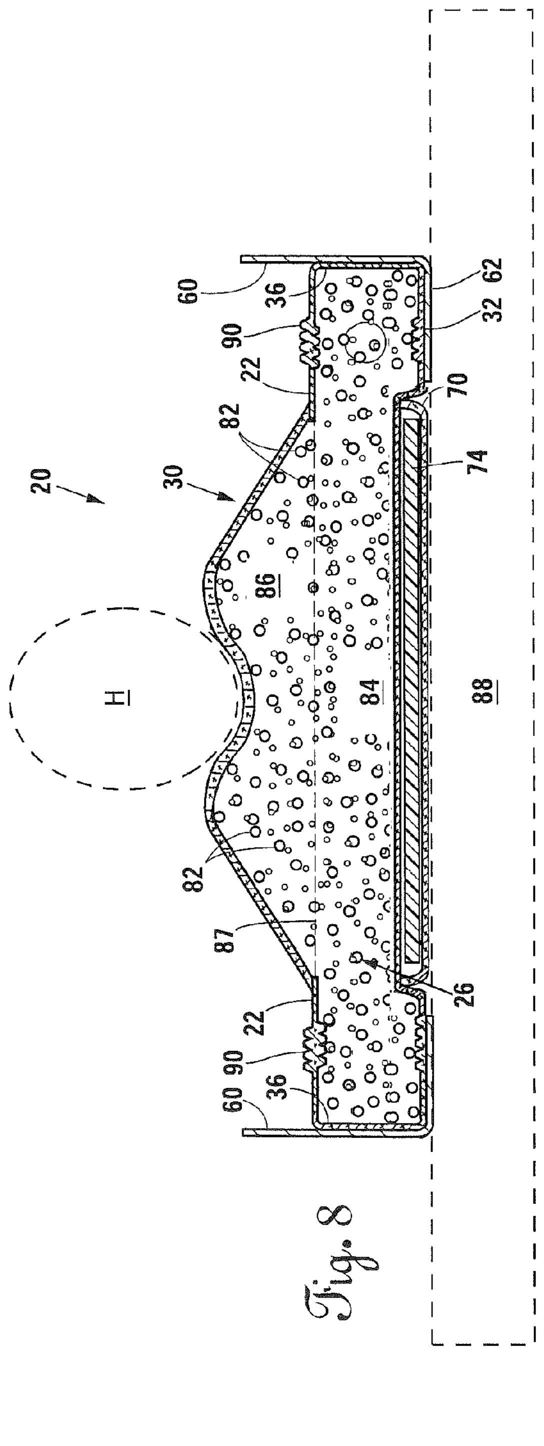
FIG. 8 is a partial sectional view of the embodiment in a fifth state.

FIG. 7-8 shows the embodiment 20 being used without the headrest 50 described with reference to FIGS. 1-6. In FIG. 7, a patient's head H is positioned directly on the support portion 30 at a first height relative to the table 88. If, upon inspection by the healthcare provider, the first height does not allow for optimal alignment of the patient's laryngeal axis, the pharyngeal axis, and the axis of the mouth for a medical procedure, the support portion 30 may be adjusted as described supra for such optimal position. For example, FIG. 8 shows the same patient's head H with the support portion 30 of the embodiment 20 having been repositioned to a second height relative to the table 88.

The present invention is described in terms of a preferred embodiment in which a specific apparatus and method is described. Those skilled in the art will recognize that alternative embodiments of such an apparatus and method can be used in carrying out the present invention. Other aspects and advantages of the present invention may be obtained from a study of this disclosure and the drawings, along with the appended claims.

I claim:

1. A height adjustable pillow for supporting a patient's head comprising:

a casing of flexible material defining a casing volume;

a base portion of said casing defining a first volume;

a support portion of said casing defining a second volume;

a volume of filler material partially occupying in said casing volume;

said first volume and said second volume being compressible and expandable;

said support portion positioned above said base portion;

an air valve associated with said casing for introducing air into and evacuating air from said casing volume;

wherein said second volume is expandable between a first magnitude when said support portion is devoid of filler material and a second magnitude when said support portion is filled with filler material; and an opening between said first volume and said second volume allowing filler material to pass between said first volume and said second volume.

2. The pillow of claim 1 wherein the filler material comprises a plurality of polystyrene beads and a plurality of plastic beads.

3. The pillow of claim 2 wherein the ratio of polystyrene beads to plastic beads is seven to three.

4. The pillow as disclosed in claim 1 comprising a base portion has a generally rectangular cuboid shape comprising a bottom and four sidewalls.

5. The pillow as disclosed in claim 1 wherein said support portion is generally frustum shaped when filled with filler material.

6. The pillow as disclosed in claim 1 further comprising a headrest having a bottom surface and at least one side surface, wherein said support portion is frictionally engaged with said bottom of said headrest.

7. The pillow as disclosed in claim 4 further comprising two side panels each positioned outside and adjacent one of opposing sidewalls.

8. The pillow as disclosed in claim 7 wherein said side panels compress said first volume of said base portion as said side panels are moved towards the center of said base portion.

9. The pillow as disclosed in claim 7 wherein a support plate positioned below and adjacent said base portion of said casing.

10. A method of adjusting and supporting the position of a patient's head with an adjustable pillow comprising:

positioning a casing below a patient's head, said casing comprising a base portion having a first volume and a support portion having a second volume;

introducing filler material into said casing;

introducing air into said casing;

compressing said first volume; and moving said filler material from said first volume into said second volume.

11. The method as disclosed in claim 10 further comprising expanding said second volume.

12. The method as disclosed in claim 10 further comprising evacuating said air from said casing.

13. The method as disclosed in claim 10 wherein said filler material comprises a plurality of polystyrene beads and a plurality of plastic beads.

14. The method as disclosed in claim 13 wherein the ratio of polystyrene beads to plastic beads is seven to three.

15. The method as disclosed in claim 10 wherein said base portion has a generally rectangular cuboid shape comprising a bottom and four sidewalls.

16. A pillow for supporting a patient's head comprising:

a casing defining an enclosed casing volume;

said casing comprising a first plurality of connected flexible pieces of material defining a base portion having a first volume and a second plurality of connected flexible pieces of material defining a support portion positioned adjacent and above said base portion and having a second volume;

an air valve attached to the casing for providing air to and from said casing volume;

filler material at least partially occupying said first volume;

said base portion being generally shaped as a partially enclosed rectangular cuboid;

said first and second volumes being compressible and expandable;

a plate positioned below said base portion of said casing and adjacent the first plurality of flexible pieces of material; and wherein said plate is positioned within a pocket.

17. A pillow for supporting a patient's head comprising:

a casing defining an enclosed casing volume;

said casing comprising a first plurality of connected flexible pieces of material defining a base portion having a first volume and a second plurality of connected flexible pieces of material defining a support portion positioned adjacent and above said base portion and having a second volume;

an air valve attached to the casing for providing air to and from said casing volume;

filler material at least partially occupying said first volume;

said base portion being generally shaped as a partially enclosed rectangular cuboid;

said first and second volumes being compressible and expandable; and wherein said second volume is expandable between a first magnitude when said support portion is devoid of filler material and a second magnitude when said support portion is filled with filler material.

* * * * *